Figure 1:
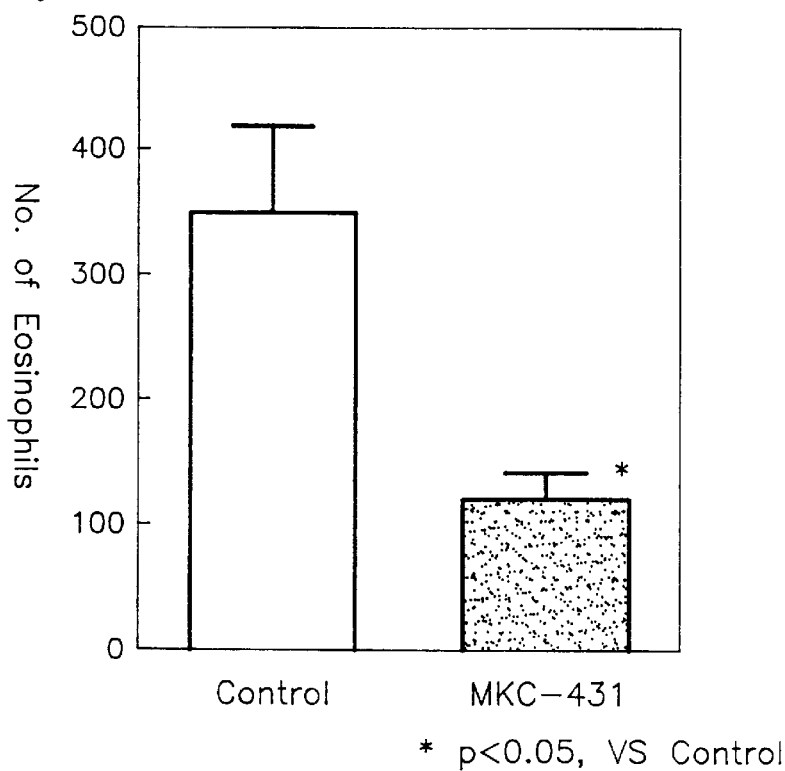

United States Patent [19]

Yamada et al.

[11] Patent Number: 5,891,884

[45] Date of Patent: Apr. 6, 1999

[54] USE OF AN IMIDAZOLE DERIVATIVE FOR PREVENTING AND/OR TREATING RHINITIS

[75] Inventors: Noboru Yamada; Fumiko Sano, both of Kanagawa, Japan

[73] Assignee: Synthelabo, Le Plessis-Robinson Cedex, France

[21] Appl. No.: 937,358

[22] Filed: Sep. 24, 1997

[30] Foreign Application Priority Data

Sep. 27, 1996 [JP] Japan .................................. 8-256624

[51] Int. Cl.$^6$ .................................................. A61K 31/505
[52] U.S. Cl. .......................................... 514/272; 514/275
[58] Field of Search ..................................... 514/272, 275

[56] References Cited

U.S. PATENT DOCUMENTS

| | | | |
|---|---|---|---|
| 4,820,710 | 4/1989 | Manoury et al. | 514/272 |
| 4,912,219 | 3/1990 | Manoury et al. | 544/321 |

FOREIGN PATENT DOCUMENTS

| | | | |
|---|---|---|---|
| 0 217 700 A1 | 4/1987 | European Pat. Off. | 515/272 |

*Primary Examiner*—Jerome D. Goldberg
*Attorney, Agent, or Firm*—Jacobson, Price, Holman & Stern, PLLC

[57] ABSTRACT

Use of a compound represented by the following general formula (I)

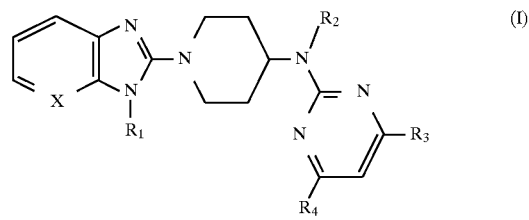

where X is a group —CH— or a nitrogen atom;

$R_1$ is a hydrogen atom, a benzyl group, a substituted benzyl group; a non-substituted heterocyclic methyl group wherein the heterocyclic part is a pyridyl, thienyl or furyl; or a substituted heterocyclic methyl group;

$R_2$ is a hydrogen atom or ($C_{1-4}$) alkyl group;

$R_3$ is a hydrogen atom or hydroxy group;

$R_4$ is a hydrogen atom or ($C_{1-4}$) alkyl group, its tautomer when $R_3$ is an hydroxy group, their pharmaceutically permissible acid addition salts, or any of their hydrates for preventing and/or treating rhinitis.

5 Claims, 1 Drawing Sheet

USE OF AN IMIDAZOLE DERIVATIVE FOR PREVENTING AND/OR TREATING RHINITIS

SPECIFICATION

The present invention relates to a preventive and/or therapeutic agent for rhinitis and, more particularly, to a preventive and/or therapeutic agent for rhinitis whose effective ingredient is an imidazole derivative of a particular structure.

Allergic rhinitis is a disease with three major symptoms of sneeze, aqueous rhinorrhea and nasal obstruction, in which type I allergic reaction participates. An increase of eosinophilia in nasal discharge is recognized in about 90% of the patients of allergic rhinitis, and eosinophils that have infiltrated to nasal tissues are known to participate in the onset of allergic rhinitis (Akimasa Miyamoto, Clinical Allergy, Nankodo, 1992.)

When antigen induction is performed on a patient of allergic rhinitis, allergic symptoms such as sneeze and rhinorrhea appear just after the antigen induction, and a feeling of nasal obstruction is observed a little later which often lasts for several hours. An increase of eosinophil count in a nasal cavity wash is observed after several hours from the antigen induction (Akiyoshi Konno, Nasal Anaphylaxis, Sakaki Co., Ltd., 1996). The reaction just after the antigen induction is referred to as immediate type reaction, and the reaction after several hours is referred to as delayed type reaction.

When an antigen is dripped into the noses of an actively sensitized guinea pig, allergic symptoms such as sneeze and sniffle appear as immediate type reactions and eosinophilic infiltration to nasal tissues is observed as a delayed type reaction as in a patient of allergic rhinitis. A sequential detection of the nasal airway resistance of the guinea pig leads to observation of a biphasic increase of nasal airway resistance with the immediate and delayed type reactions (Akiyoshi Konno, Nasal Anaphylaxis, Sakaki Co., Ltd., 1996). Thus it has been revealed that an immediate type reaction and delayed type reaction occur by antigen induction and an eosinophilic infiltration to nasal tissues follows with the delayed type reaction both in a patient of allergic rhinitis and an animal model.

In clinical studies, fluticasone propionate which is a local steroid drug is reported as a drug to inhibit the eosinophilic infiltration to nasal tissues accompanying with a delayed type reaction (Akiyoshi Konno, Nasal Anaphylaxis, Sakaki Co., Ltd., 1996). A steroid drug, however, cannot avoid adverse drug reactions such as body weight gain, edema, hyperorexia and hypertension, and a new drug with few of these adverse reactions that inhibits the eosinophilic infiltration to nasal tissues associating with the delayed type reaction has been desired.

The European Patent EP 0 217 700 describes imidazol derivatives which have a histamine antagonistic action and can be used for therapy of various allergic symptoms such as respiratory allergy, cutaneous allergy and ocular allergy, and that these compounds have no anticholin and antiserotonin actions. A compound described in the European Patent EP 0 217 700, 2-([1-{1-[(4-fluorophenyl)methyl]-1H-benzimidazol-2-yl}-4-piperidyl]methylamino)-4-pyrimidinol (generic name: mizolastine), is an antiallergic drug with little central nervous system depressant action which has an antihistamic action characterized in that the drug has both the histamine antagonistic action and chemical mediator antireleaser action in a good balance and that its central nervous system depressant action is very weak (Benavides J. et al., Arzneim Forsch/Drug Res 45, 551–558, 1995, Levrier J. et al., Arzneim Forsch/Drug Res 45, 559–568, 1995). However, it has not been reported, so far as the present inventors know, that these compounds have any inhibitory action on eosinophilic infiltration to nasal tissues and that they have any inhibitory action not only on an immediate type reaction but also on a delayed type reaction of allergic reactions.

The present invention has been constituted for the object of providing an excellent preventive and/or therapeutic agent for rhinitis with little central nervous system depressant action.

The present inventors investigated to resolve the above problem, and as a result, we found that a kind of imidazole derivatives can be an excellent preventive and/or therapeutic agent for rhinitis with little central nervous system depressant action which have an inhibitory action on eosinophilic infiltration to nasal tissues in a delayed type reaction, and we have completed the present invention.

The preventive and/or therapeutic agent for rhinitis of the present invention contains a compound represented by the following general formula (I)

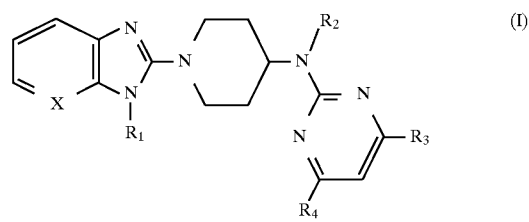

where X is a group —CH— or a nitrogen atom;

$R_1$ is a hydrogen atom, a non-substituted benzyl group, a benzyl group substituted by up to three substitutional groups selected from the group consisting of halogen, trifluoromethyl, $(C_{1-4})$ alkyl, $(C_{1-4})$ alkoxy, cyano, methylthio, methylsulfinyl or methylsulfonyl groups; a non-substituted heterocyclic methyl group wherein the heterocyclic part is a pyridyl, thienyl or furyl; or a heterocyclic methyl group wherein the heterocyclic part is substituted by one or more substitutional groups selected from the group consisting of halogen, trifluoromethyl, $(C_{1-4})$ alkyl, $(C_{1-4})$ alkoxy, cyano, methylthio, methylsulfinyl or methylsulfonyl groups;

$R_2$ is a hydrogen atom or $(C_{1-4})$ alkyl group;

$R_3$ is a hydrogen atom or hydroxy group;

$R_4$ is a hydrogen atom or $(C_{1-4})$ alkyl group.

The free form of compounds described above, their pharmaceutically permissible acid addition salts, or any of their hydrates can be used as an effective ingredient of the preventive and/or therapeutic agent of the present invention.

Some examples for the pharmaceutically permissible acid addition salts are inorganic acid salts such as hydrochlorides, hydrobromides, sulfates, phosphates and nitrates; and organic acid salts such as acetates, succinates, adipates, propionates, tartrates, fumarates, maleates, oxalates, citrates, benzoates, toluenesulfonates and methanesulfonates.

A preferable compound of the formula (I) above is a compound whose X is a group —CH— or nitrogen atom, $R_1$ is 4-fluorobenzyl group, and $R_2$, $R_3$ and $R_4$ are compounds which have the same significance as above.

Among the compounds of the formula (I) whose X is a group —CH—, preferable compounds are those whose $R_1$ is a benzyl group which has one or two substitutional groups, particularly one substitutional group at the 4-site which is a fluorine or chlorine atom or a methyl, methoxy, methylthio, trifluoromethyl, cyano or methylsulfinyl group.

If $R_3$ is a hydroxy group and $R_4$ is a hydrogen atom, these compounds can exist in tautomeric forms which are part of the invention.

Concrete examples for preferable compounds among these ones are those described in European Patent No. EP 0 217 700 and the most preferable one is 2-([1-{1-[(4-fluorophenyl)methyl]-1H-benzimidazol-2-yl}-4-piperidyl] methylamino)-4-pyrimidinol (herein below sometimes referred to as "mizolastine" or "MKC-431").

The compound represented by the above general formula (I) which is an effective ingredient of the preventive and/or therapeutic agent for rhinitis of the present invention described above is a known compound described in European Patent EP 0 217 700, and it can readily be manufactured in accordance with the description of the application.

The above-mentioned compound itself which is an effective ingredient may be used as the preventive and/or therapeutic agent for rhinitis of the present invention, but it is preferable to use medical composites comprising the above effective ingredient manufactured by using common additives for pharmaceutical preparations. Some examples for such medical composites are tablets, capsules, granules, balls or pills, troches, liquid drugs, injections, suppositories, ointments and poultices, which are orally (including sublingual administration) or non-orally administered.

The medical composite for oral use can be manufactured by conventional all-purpose methods such as mixing, packing or tablet making. The effective ingredient may be distributed in a medical composite using a large amount of filler by using a repetitive blending. For example, a tablet or capsule used for the oral administration is preferably provided as a unit dose which may contain a carrier, generally used for pharmaceutical preparation, such as a binder, filler, diluent, tableting agent, lubricant, disintegrator, coloring agent, flavoring agent and infiltrating agent. Tablets may be prepared following methods known in the art, for example, they may be coated tablets using a coating agent.

Some examples for a preferable filler are cellulose, mannitol and lactose, and starch and polyvinyl pyrrolidone which are disintegrators, starch derivatives such as sodium starch glycolate and dodecyl sodium sulfate which is a lubricant may be used as additives for the pharmaceutical preparation. The medical composites for oral administration in the form of liquid drugs are provided, for example, as aqueous or oily suspension, solution, emulsion, medical composites such as syrup or elixir, or dry medical composites redissolved with water or other suitable media before use.

To such liquid drugs, general additives, e.g. suspending agent such as sorbitol, syrup, methylcellulose, gelatin, hydroxyethylcellulose, carboxymethylcellulose, aluminium stearate gel or hydrogenated edible fat; emulsifying agents such as lecithin, sorbitan monooleate and gum arabic; oily esters such as almond oil, rectified coconut oil, glycerin ester; nonaqueous solvents such as propylene glycol and ethyl alcohol (also includable of edible oil); preservatives such as methyl ester, ethyl ester or propyl ester of p-hydroxybenzoic acid or sorbic acid, and common flavoring agents or coloring agents can be blended where necessary.

As the medical composites suitable for non-oral administration, liquid medical composites or medical composites in a form of suppository or cataplasm which contain above-mentioned effective ingredient and sterilized media can be manufactured. For example, the effective ingredient may be suspended, dissolved or emulsified depending on the medium and concentration, e.g. the solution composites for non-oral use can preferably be manufactured by dissolving the effective ingredient in a medium and filtering the solution to sterilize, then filling it into suitable vials or ampules and sealing. Water may be removed by freeze drying after preparing the aqueous solution composite for increasing the stability.

Suspensions for non-oral use are manufactured by substantially the same method as that for the solution composites for non-oral use described above. For example, they are manufactured by suspending the effective ingredient in a medium, sterilizing using ethylene oxide, etc., and further suspending in a sterilized medium. Surfactants or lubricants may be added, where necessary, on manufacturing the suspensions, etc. to make the effective ingredient uniformly distributed in the pharmaceutical preparations. The medical composites in other forms can also be manufactured by methods known to those skilled in the art, and the form and method for manufacturing of the medical composite which is one aspect of the drug of the present invention are not limited to those mentioned above.

The above-mentioned medical composites for oral use, e.g. tablets, capsules and granules generally contain 0.1–95 percentage by weight, preferably 0.5–10 percentage by weight of the effective ingredient, while the medical composites for non-oral use, e.g. injections generally contain 0.05–40 percent by weight, preferably 0.1–20 percent by weight of the effective ingredient.

The preventive and/or therapeutic agent for rhinitis of the present invention has an inhibitory action on eosinophilic infiltration to nasal tissues, and it is useful for prevention and/or therapy of rhinitis such as allergic rhinitis, vasomotor rhinitis or rhinitis with eosinophilia.

According to a preferred embodiment of the present invention, said preventive and/or therapeutic agent for rhinitis is provided wherein the compound represented by said formula (I) is 2-([1-{1-[(4-fluorophenyl)methyl]-1H-benzimidazol-2-yl}-4-piperidyl]methylamino)-4-pyrimidinol; said preventive and/or therapeutic agent for rhinitis wherein the rhinitis is allergic rhinitis; said preventive and/or therapeutic agent for rhinitis wherein the allergy is a delayed type allergy and said preventive and/or therapeutic agent for rhinitis wherein the prevention and/or therapy is due to an inhibitory action on eosinophilic infiltration to nasal tissues.

The dose of the preventive and/or therapeutic agent for rhinitis of the present invention may be fitly decided in accordance with the age, condition of health, weight, severity of disease, sorts and frequency of the therapy or treatment simultaneously performed, and nature of desired effect, etc. of patients. Generally, one dose for an adult may be 0.01–100 mg/kg-weight, preferably 0.1–10 mg/kg-weight as the amount of the effective ingredient and the drug may be administered once to a few times daily.

The present invention will be particularly described with embodiments, which the present invention is not limited to.

Mizolastine, used in the embodiments below, (2-([1-{1-[(4-fluorophenyl)methyl]-1H-benzimidazol-2-yl}-4-piperidyl]methylamnino)-4-pyrimidinol)was prepared in accordance with the method described in the European Patent No. 0 217 700.

EXAMPLE 1

Inhibitory action on eosinophilic infiltration to nasal tissues and inhibitory action on a delayed type reaction of mizolastine.

The inhibitory action on eosinophilic infiltration to nasal tissues and inhibitory action on a delayed type reaction of mizolastine were studied following the method described by Shin-ichiro Narita et al., Int. Arch. Allergy. Immunol., 109, 161–166 (1996).

Ovalbumin and aluminium hydroxide gel were administered i.p. three times every two weeks to Hartley male guinea pigs. Further, ovalbumin was inhaled with a nebulizer (made by Mizuho Medical Industries) for local sensitization to actively sensitive the guinea pigs every day for two weeks.

Ovalbumin was dripped into both sides of nasal cavities of actively sensitized guinea pigs, and after four hours the guinea pigs were subjected to anaesthesia and exsanguinations, then the noses were extirpated. The noses were fixed with 10% formalin, then delimed to prepare nasal tissue sections, which were stained with Luna staining and the number of eosinophil leukocytes infiltrated to nasal tissues was counted.

Ovalbumin was also dripped into both sides of nasal cavities of actively sensitized guinea pigs and the change of nasal airway resistance was measured up to six hours after the nasal instillation of antigen. The nasal airway resistance was measured by an oscillation method (Shin-ichiro Narita et al., Int. Arch. Allergy. Immunol., 100, 373–377 (1993) using a body plethysmograph for small animals (made by Syzmedical).

In any of the cases, mizolastine was suspended in 1% tragacanth solution and 3 mg/kg was administered orally one hour before the antigen challenge. In a control group, 1% tragacanth solution was administered orally.

Antigen was instilled into the nose of actively sensitized guinea pigs, and 349170 eosinophil leukocytes were observed to infiltrate to nasal tissues after four hours from the antigen instillation. Mizolastine inhibited the eosinophilic infiltration to nasal tissues (FIG. 1).

Figure 2:
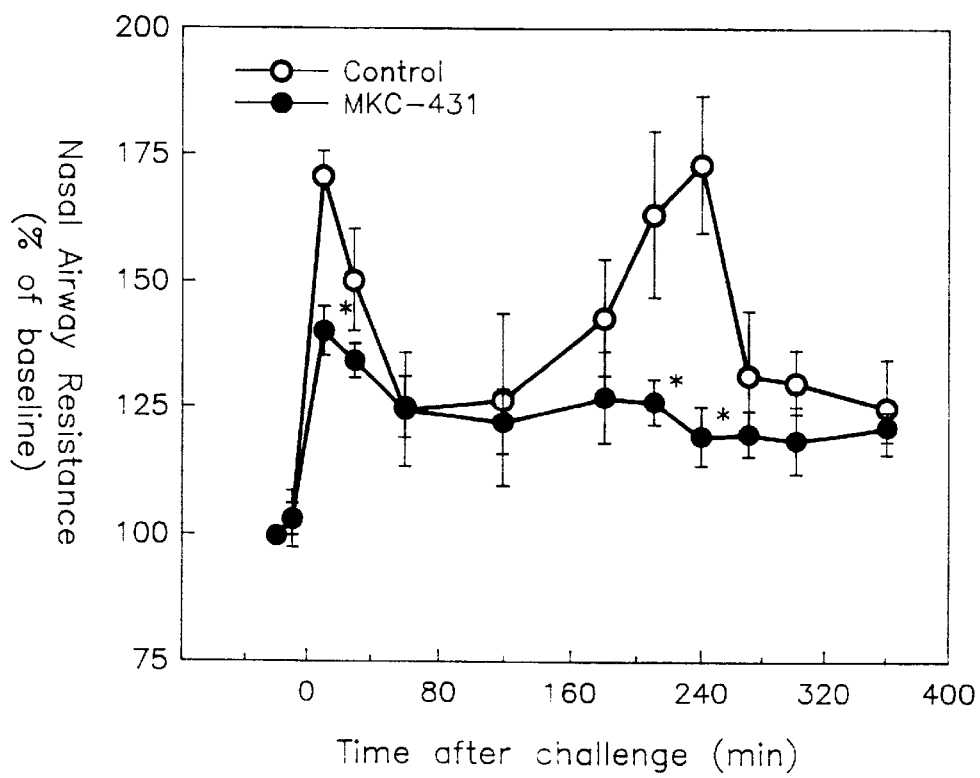

When antigen is dripped into the nose of actively sensitized guinea pigs, increases of nasal airway resistance are observed just after the antigen instillation (immediate type reaction) and after several hours from the antigen instillation (delayed type reaction). Mizolastine inhibited the immediate and delayed type reactions due to nasal antigen instillation (FIG. 2).

Advantages of the Invention

The imidazole derivatives represented by the general formula (I) have an inhibitory action on eosinophilic infiltration to nasal tissues, and they have an inhibitory action not only on an immediate type reaction but also on a delayed type reaction of allergic reactions. The compound of the present invention therefore is effective as a preventive and/or therapeutic agent for rhinitis with little central nervous system depressant action. Furthermore, this agent is also expected to have a clinical effect on nasal obstruction because a delayed type reaction is clinically affinitive to nasal obstruction.

FIG. 1 is a graphical representation showing the inhibitory action on eosinophilic infiltration to nasal tissues, the axis of ordinates indicating the number of eosinophils. In the representation, Control indicates the control group and MKC-431 indicates the mizolastine administration group.

FIG. 2 is a graphical representation showing the inhibitory action on the immediate and delayed type reactions due to nasal antigen instillation, the axis of ordinates indicating the nasal airway resistance (percentage of change by value before nasal antigen instillation) and the axis of abscissas indicating the time after the nasal antigen instillation (minute). In the representation, Control indicates the control group and MKC-431 indicates the mizolastine administration group.

We claim:

1. A method for preventing and/or treating vasomotor rhinitis comprising administering to a host in need of said method an effective amount of a compound represented by the following general formula (I):

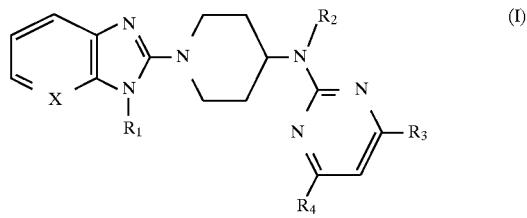

where X is a —CH— group or a nitrogen atom;

$R_1$ is a hydrogen atom, a non-substituted benzyl group, a benzyl group substituted by up to three substitutional groups selected from the group consisting of halogen, trifluoromethyl, ($C_{1-4}$) alkyl, ($C_{1-4}$) alkoxy, cyano, methylthio, methylsulfinyl and methylsulfonyl groups; a non-substituted heterocyclic methyl group wherein the heterocyclic part is a pyridyl, thienyl or furyl; or a heterocyclic methyl group wherein the heterocyclic part is substituted by one or more substitutional groups selected from the group consisting of halogen, trifluoromethyl, ($C_{1-4}$) alkyl, ($C_{1-4}$) alkoxy, cyano, methylthio, methylsulfinyl and methylsulfonyl groups;

$R_2$ is a hydrogen atom or ($C_{1-4}$) alkyl group;

$R_3$ is a hydrogen atom or hydroxy group;

$R_4$ is a hydrogen atom or ($C_{1-4}$) alkyl group, its tautomer when $R_3$ is an hydroxy group, their pharmaceutically permissible acid addition salts, or any of their hydrates.

2. The method according to claim 1 wherein said compound is 2-([1-{1-[(4-fluorophenyl)methyl]-1H-benzimidazol-2-yl}-4-piperidyl]methylamino)-4-pyrimidinol.

3. The method according to claim 1 wherein the vasomotor rhinitis is rhinitis with eosinophilia.

4. The method according to claim 1 wherein said rhinitis is caused by an eosinophilia infiltration into nasal tissue.

5. The method according to claim 1 wherein the vasomotor rhinitis is a rhinitis with nasal airway resistance.

* * * * *